(12) United States Patent
Suzuki

(10) Patent No.: US 9,215,971 B2
(45) Date of Patent: Dec. 22, 2015

(54) ENDOSCOPE

(71) Applicant: OLYMPUS CORPORATION, Tokyo (JP)

(72) Inventor: Norihisa Suzuki, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/163,474

(22) Filed: Jan. 24, 2014

(65) Prior Publication Data

US 2014/0142388 A1     May 22, 2014

Related U.S. Application Data

(63) Continuation of application No. PCT/JP2013/060685, filed on Apr. 9, 2013.

(30) Foreign Application Priority Data

Jun. 6, 2012   (JP) .................................. 2012-129184

(51) Int. Cl.
| | |
|---|---|
| *A61B 1/04* | (2006.01) |
| *A61B 1/008* | (2006.01) |
| *A61B 1/00* | (2006.01) |
| *G02B 23/24* | (2006.01) |
| *A61B 1/005* | (2006.01) |

(52) U.S. Cl.
CPC ............... *A61B 1/008* (2013.01); *A61B 1/0008* (2013.01); *A61B 1/0011* (2013.01); *A61B 1/0055* (2013.01); *A61B 1/00071* (2013.01); *G02B 23/2476* (2013.01); *A61B 1/005* (2013.01)

(58) Field of Classification Search
USPC .......................... 600/127–130, 141, 175, 920
See application file for complete search history.

(56) References Cited

U.S. PATENT DOCUMENTS

| | | | |
|---|---|---|---|
| 4,726,355 A | 2/1988 | Okada | |
| 5,454,366 A * | 10/1995 | Ito et al. ......................... | 600/109 |
| 6,183,182 B1 * | 2/2001 | Baumgartner ................. | 411/533 |

FOREIGN PATENT DOCUMENTS

| | | |
|---|---|---|
| JP | H06-142032 A | 5/1994 |
| JP | 10-043130 A | 2/1998 |

(Continued)

OTHER PUBLICATIONS

Extended Supplementary European Search Report dated Feb. 16, 2015 received in corresponding European Patent Application No. 13800939.4.

*Primary Examiner* — Matthew J Kasztejna
(74) *Attorney, Agent, or Firm* — Scully, Scott, Murphy & Presser, P.C.

(57) ABSTRACT

An insertion portion includes a holding member that holds an observation portion, and a tubular bending portion. A small-diameter portion of the holding member is fitted into an inside surface of a distal end side portion of the bending portion. A hole portion is provided in the bending portion. A concave portion is provided at the small-diameter portion. A screw member penetrates the hole portion by screw-fastening, and a distal end side thereof is housed in the concave portion. A diameter of the concave portion is larger than an outside diameter of the screw member. A length obtained by adding a depth of the concave portion and a thickness of the distal end side portion of the bending portion is greater than an axial direction length of the screw member. The screw member is held in a non-contacting state with respect to the concave portion in the hole portion.

6 Claims, 4 Drawing Sheets

(56) References Cited

FOREIGN PATENT DOCUMENTS

| JP | 10-192219 A | 7/1998 |
| JP | 2000-241718 A | 9/2000 |
| JP | 2000-271071 A | 10/2000 |
| JP | 2002-034895 A | 2/2002 |
| JP | 2003-262209 A | 9/2003 |
| JP | 2003-325527 A | 11/2003 |
| JP | 2006226465 A | 8/2006 |

* cited by examiner

ENDOSCOPE

CROSS REFERENCE TO RELATED APPLICATION

This application is a continuation application of PCT/JP2013/060685 filed on Apr. 9, 2013 and claims benefit of Japanese Application No. 2012-129184 filed in Japan on Jun. 6, 2012, the entire contents of which are incorporated herein by this reference.

BACKGROUND OF THE INVENTION

1. Field of the Invention

The present invention relates to an endoscope in which a distal end portion is attached at a position that is further on a distal end side than a bending portion that has a tubular structure.

2. Description of the Related Art

In some endoscopes, a bending portion that is configured so as to be capable of bending is provided in an insertion portion. In an endoscope capable of bending in this manner, a rigid distal end portion that has an observation portion for observing an observation site (observation object) is disposed at a position that is further on a distal end side than the bending portion.

Conventionally, a screw or the like has been used to connect the distal end portion and the bending portion in such endoscopes.

For example, in FIG. 1 and paragraph [0014] of Japanese Patent Application Laid-Open Publication No. 2003-325527, it is described that a joint ring (21) at a distalmost end that is included in a bending portion (2) is fitted in the vicinity of a rear end of a distal end portion body (3) and is coupled thereto by means of a small screw (22).

Further, in FIG. 6 and paragraph [0013] of Japanese Patent Application Laid-Open Publication No. 2002-034895, it is described that a portion close to the rear of a distal end portion body (5) is fitted into a portion close to the tip of a joint ring (31a) located at a distalmost end of a bending portion (3) and is fixed thereto with a screw.

In addition, in FIGS. 1 and 3 and paragraph [0014] of Japanese Patent Application Laid-Open Publication No. 10-192219, it is described that a distal end portion body (31) and a bending portion (32) are connected by screwing a joint ring (33) that is at a distalmost end to a pair of screw pieces (37) made of metal that are embedded in a concave portion of the distal end portion body (31) and in which a female screw thread is threaded.

In this connection, for example, in an endoscope that is compatible with high frequency treatment or the like, in order to form a structure that electrically insulates an endoscope distal end portion from a living organism, in some cases a resin is used as a material for forming the distal end portion. When connecting a bending portion and a distal end portion that is made of resin, the bending portion and the distal end portion made of resin are fixed together by means of an adhesive.

SUMMARY OF THE INVENTION

An endoscope according to a certain aspect of the present invention includes: an insertion portion that is insertable into an observation object; a bending portion having a bendable tubular structure that is provided in the insertion portion; a holding member that is provided at a position that is further on a distal end side than the bending portion, and is used for holding an observation portion that observes the observation object; a contact portion that is positioned in a distal end side portion of the bending portion, and that contacts a proximal end side portion of the holding member as a result of the proximal end side portion of the holding member being fitted into an inside surface thereof; a hole portion that is positioned at the contact portion, and is provided in the proximal end side portion of the bending portion; a concave portion that is provided at a position corresponding to the hole portion in the proximal end side portion of the holding member; and a screw member that penetrates the hole portion by screw-fastening, and whose distal end side is housed in the concave portion; in which: a diameter in a plane perpendicular to a depth direction of the concave portion is larger than an outside diameter of the screw member, and a length obtained by adding a depth of the concave portion and a thickness of the distal end side portion of the bending portion is greater than an axial direction length of the screw member; and the screw member is held in a non-contacting state with respect to the concave portion in the hole portion.

DETAILED DESCRIPTION OF THE PREFERRED EMBODIMENTS

Embodiments of the present invention are described hereunder with reference to the drawings.

[First Embodiment]

Figure 1:
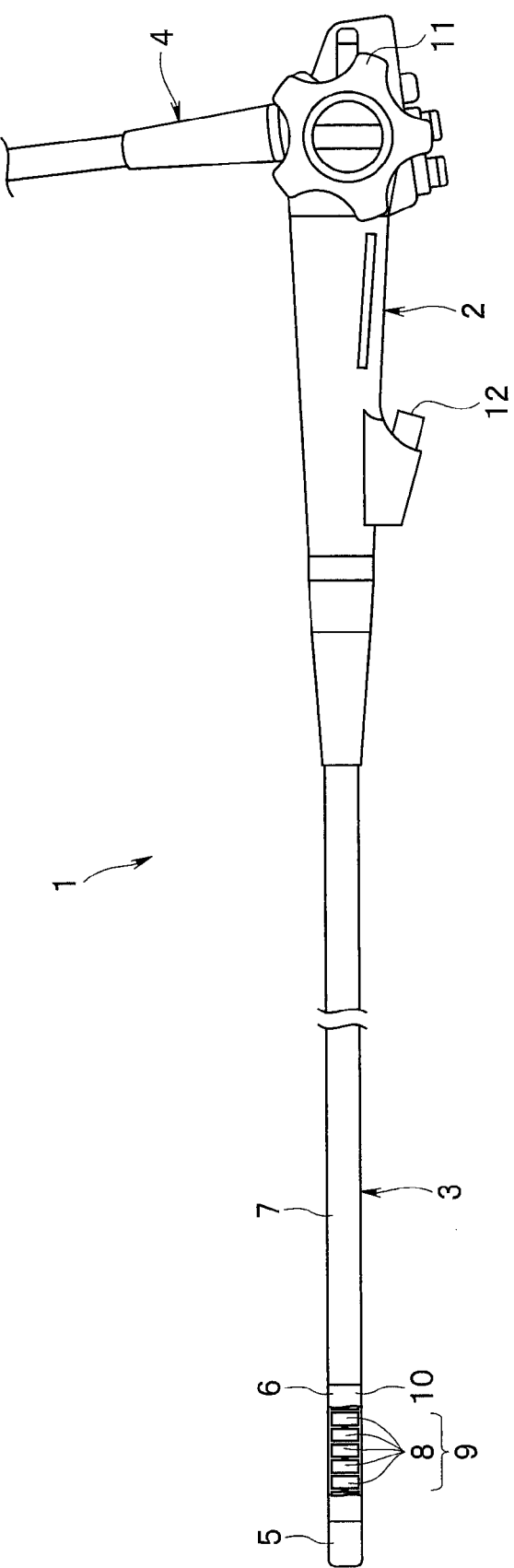
FIG. 1 is a side view that illustrates a configuration of an endoscope according to a first embodiment of the present invention.
Figure 2:
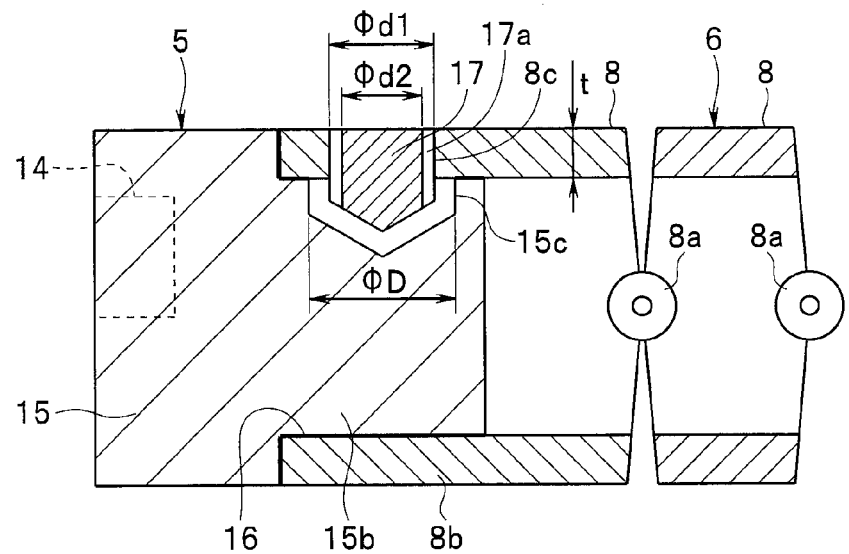
FIG. 2 is a cross-sectional view that illustrates a connection structure between a distal end side portion of a bending portion and a distal end portion in the first embodiment.
Figure 3:
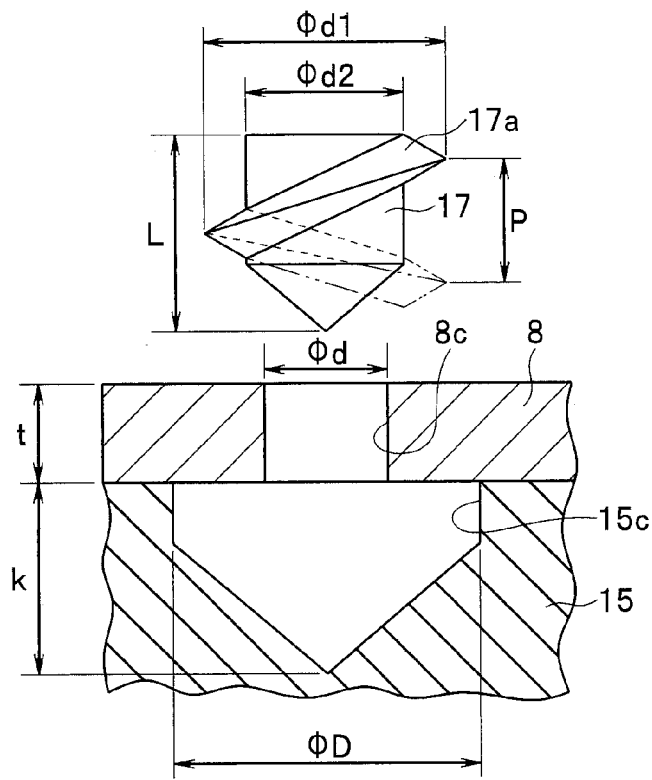
FIG. 3 is a view for describing the relationship between the dimensions of a screw member, a hole, and a concave portion in the first embodiment.

FIG. 1 to FIG. 3 illustrate a first embodiment of the present invention. FIG. 1 is a side view that illustrates the configuration of an endoscope.

Although an endoscope 1 may be any one of an electronic endoscope, an optical endoscope, an ultrasound endoscope or the like, hereunder a case in which the endoscope 1 is an electronic endoscope is described as an example.

As shown in FIG. 1, the endoscope 1 includes an operation portion 2, an elongated insertion portion 3 that extends from the operation portion 2, and a universal cord 4 that extends from a side face of the operation portion 2.

The insertion portion 3 is a part that is insertable into an observation site (observation object) that is an examination object. In the case of a medical endoscope the insertion portion 3 is inserted into, for example, a body cavity of a subject (living organism) that is an observation site (observation object), while in the case of an industrial endoscope the insertion portion 3 is inserted into, for example, an engine that is an observation site (observation object).

The insertion portion 3 includes a distal end portion 5 that is provided on a distal end side, a bendable bending portion 6 that is connected to the proximal end of the distal end portion 5, and a flexible portion 7 that is connected to a proximal end of the bending portion 6 and has flexibility.

An observation portion 14 (see FIG. 2) for observing an observation site (observation object), and a holding member 15 (see FIG. 2) for holding the observation portion 14 and which is formed of an insulating material such as, for example, a resin are arranged in the distal end portion 5. The observation portion 14 includes, for example, an objective lens for forming an optical image of an observation site (observation object), and an image pickup device that performs photoelectric conversion of the optical image formed by the objective lens and outputs a resulting signal as an image signal. The image signal that is outputted from the image pickup device is transmitted through the insertion portion 3, the operation portion 2, and an image pickup cable arranged inside the universal cord 4 to a CCU (camera control unit), which is not shown in the drawings, to which the universal cord 4 is connected, and is displayed as an endoscopic image on a monitor or the like, which is not shown in the drawings, that is connected to the CCU.

An illuminating window, for example, is provided in the distal end portion 5. An illuminating light from a light source apparatus, which is not shown in the drawings and which is connected to the universal cord 4, is guided to the illuminating window through a light guide fiber that is arranged in the universal cord 4, the operation portion 2, and the insertion portion 3, and is irradiated at the observation site (observation object) from the illuminating window.

An opening of a channel that serves both as a forceps channel and an air/water feeding channel is also provided in the distal end portion 5. The endoscope 1 is configured so that a fluid from an air/water feeding apparatus, which is not shown in the drawings and which is connected to the universal cord 4, is supplied to the distal end portion 5 through a channel tube arranged in the universal cord 4, the operation portion 2, and the insertion portion 3, or so that a forceps is inserted through the distal end portion 5 from a forceps insertion port 12 provided in the operation portion 2 via a channel tube inside the insertion portion 3.

The bending portion 6 is configured so as to form a tubular structure so that the above described image pickup cable, light guide fiber; and channel tube and the like can be inserted through the inside thereof. Specifically, the bending portion 6 includes a bending tube 9 that is constituted by a plurality of joint rings 8 that are connected in series so as to be rotatable, and an angle rubber 10 that has flexibility and covers the outer circumference of the bending tube 9. Among the plurality of joint rings 8 constituting the bending tube 9, the joint ring 8 that is located at a position that is furthest on the distal end side (hereunder, may be referred to as "first joint ring 8" as appropriate) is fixed to the distal end portion 5.

The distal ends of angle wires are fixed to the distal end portion 5, and the proximal ends of the angle wires that are inserted through the inside of the insertion portion 3 are connected to a pulley that rotates in response to movement of an angle knob 11 that is provided on the operation portion 2. The configuration is such that when the angle knob 11 is operated, one of the angle wires that form a pair is tensed and the other of the angle wires relaxes so that the bending portion 6 bends and the direction of the distal end portion 5 can be changed.

FIG. 2 is a cross-sectional view that illustrates a connection structure between the distal end side portion of the bending portion 6 and the distal end portion 5.

Each of the joint rings 8 includes a joint ring body 8b that has a short cylindrical shape (tube shape). The bending tube 9 is constituted by rotatably connecting a plurality of the joint ring bodies 8b through connection portions 8a. The first joint ring 8 at the distalmost end and a second joint ring 8 that is next after the first joint ring 8 are illustrated in FIG. 2.

A hole 8c that is perpendicular to the axial direction of the insertion portion 3 is formed in the joint ring body 8b of the first joint ring 8 (that is, the distal end side portion of the bending portion 6).

A concave portion 15c is provided at a position corresponding to the hole 8c of the first joint ring 8 in a small-diameter portion 15b of the proximal end side portion of the holding member 15.

After the small-diameter portion 15b of the proximal end side portion of the holding member 15 is fitted into the inside surface of the tubular structure of the first joint ring 8 and alignment between the hole 8c and the concave portion 15c is performed, portions at which the holding member 15 and the first joint ring 8 contact each other (that is, contact portions between the distal end portion 5 and the bending portion 6) are joined and fixed by means of an adhesive 16.

Thereafter, connection of the distal end side portion of the bending portion 6 and the distal end portion 5 is performed by screw-fastening a screw member 17 which has a screw thread 17a that is threaded on the circumferential surface thereof into the hole 8c to cause the screw member 17 to penetrate the hole 8c so that a distal end side thereof is housed inside the concave portion 15c and the head of the screw member 17 is flush with the outer circumferential surface of the first joint ring 8.

FIG. 3 is a view for describing the relationship between the dimensions of the screw member 17, the hole 8c, and the concave portion 15c.

The thickness of a portion of the joint ring body 8b in which the hole 8c is formed (that is, the thickness of the distal end side portion of the bending portion 6 in which the hole 8c is provided) is taken as "t" and the maximum diameter of the hole 8c as "$\Phi d$". Here, in a case where the hole 8c is a circular hole, the maximum diameter is the diameter of the hole (refer to the second embodiment that is described later with regard to a case where the hole 8c is not a circular hole).

The concave portion 15c is formed, for example, as a circular hole (however, the concave portion 15c is not limited to a circular hole), and the diameter thereof in a plane perpendicular to the depth direction is taken as "$\Phi D$" and the depth is taken as "k".

In addition, an axial direction length of the screw member 17 is taken as "L", the outside diameter of the screw thread 17a is taken as "$\Phi d1$", a root diameter of the screw thread 17a is taken as "$\Phi d2$", and a pitch of the screw thread 17a is taken as "P".

At this time, the axial direction length L of the screw member 17 is greater than the thickness t of the joint ring body 8b at the portion in which the hole 8c is provided, and the relationship of the following expression (1) is established.

$$t < L \qquad \text{[Expression 1]}$$

By adopting a configuration so as to satisfy the relationship of expression (1), because the distal end side of the screw member 17 will be housed inside the concave portion 15c, the distal end portion 5 can be prevented from dropping out even if the distal end portion 5 enters a movable state with respect to the bending portion 6 due to deterioration of the adhesive 16 or the like.

Note that, even if the above expression (1) is not satisfied it is possible to prevent the distal end portion 5 from dropping out as long as the distal end side of the screw member 17 is housed within the concave portion 15c when the screw member 17 is screw-fastened into the hole 8c. However, because the screwing length between the screw member 17 and the hole 8c becomes shorter when t≥L, it is preferable to adopt a configuration that satisfies the foregoing expression (1).

In addition, the diameter $\Phi D$ of the concave portion 15c is larger than the outside diameter $\Phi d1$ of the screw thread 17a, and the relationship of the following expression (2) is established.

$$\Phi D > \Phi d1 \qquad \text{[Expression 2]}$$

By adopting a configuration so as to satisfy the relationship of expression (2), as shown in FIG. 2, the screw member 17 and the concave portion 15c can be placed in a non-contacting state when external stress is not applied to the distal end portion 5 or the bending portion 6.

In addition, the axial direction length L of the screw member 17 is less than a length obtained by adding together the thickness t of the joint ring body 8b of the portion in which the hole 8c is provided and the depth k of the concave portion 15c, and the relationship of the following expression (3) is established.

$$L < (t+k) \qquad \text{[Expression 3]}$$

By adopting a configuration so as to satisfy the relationship of expression (3), a non-contacting state can be maintained between the screw member 17 and the concave portion 15c even when the screw member 17 is screw-fastened as far as a position (see FIG. 2) at which the head of the screw member 17 becomes flush with the outer circumferential surface of the first joint ring 8.

In addition, the maximum diameter $\Phi d$ of the hole 8c is smaller than the root diameter $\Phi d2$ of the screw thread 17a, and the relationship of the following expression (4) is established.

$$\Phi d < \Phi d2 \qquad \text{[Expression 4]}$$

By adopting a configuration so as to satisfy the relationship of expression (4), the screw member 17 will be forcibly inserted into the hole 8c and thus the fastening of the screw member 17 to the bending portion 6 will be more secure. According to the present embodiment a female screw thread is not provided in the hole 8c so that forcible insertion of the screw member 17 can be performed and also because if the insertion portion 3 has a small diameter the thickness t will also be small and micromachining will be difficult. However, a configuration may also be adopted in which a female screw thread is provided in the hole 8c.

Thus, although the screw member 17 is firmly fixed with respect to the bending portion 6, at a normal time the screw member 17 does not contact the holding member 15 that is formed of resin or the like of the distal end portion 5.

On the other hand, even when external stress is applied to the distal end portion 5 or the bending portion 6, because the adhesive 16 is used to join the distal end portion 5 and the bending portion 6 to each other at the contact portions therebetween, the distal end portion 5 does not separate from the bending portion 6.

However, in a case where disinfecting and sterilizing of the endoscope 1 has been repeatedly performed, it is also conceivable that deterioration of the adhesive will occur and a state will be entered in which the distal end portion 5 is not adhesively fixed to the bending portion 6. Even in this case, the distal end side of the screw member 17 is engaged in the concave portion 15c and thus separation of the distal end portion 5 from the bending portion 6 can be prevented.

Note that although the pitch P of the screw thread 17a may be greater or smaller than, or equal to, the thickness t of the joint ring body 8b, FIG. 3 illustrates an example in which P>t.

Further, the effects of the above described configuration can be widely exerted not only when the holding member 15 of the distal end portion 5 is formed of resin, but also when the holding member 15 is formed of a material with respect to which there is a possibility of cracks occurring.

According to the endoscope 1 of the first embodiment as described above, by forming the distal end portion 5 using an insulating material such as a resin, it is possible to electrically insulate the distal end portion 5 with respect to an observation site (observation object) such as a living organism.

Further, since a configuration is adopted so that the distal end side of the screw member 17 is housed in the concave portion 15c, separation of the distal end portion 5 from the bending portion 6 can be prevented.

In addition, since the configuration is such that, at a normal time, the screw member 17 enters a non-contacting state with respect to the holding member 15, even if the distal end portion 5 is formed of a material with respect to which there is a possibility of cracks occurring, such as a resin, cracks are not generated in the distal end portion 5.

Furthermore, since portions where the distal end portion 5 and the bending portion 6 contact each other are joined by the adhesive 16, a non-contact state between the screw member 17 and the holding member 15 is maintained at a time of normal use, and stress is not applied from the screw member 17 to the distal end portion 5.

In addition, since the maximum diameter $\Phi d$ of the hole 8c is made smaller than the root diameter $\Phi d2$ of the screw thread 17a, the screw member 17 can be firmly fastened to the bending portion 6.

Furthermore, since a configuration is adopted so that the head of the screw member 17 becomes flush with the outer circumferential surface of the bending portion 6 when the small-diameter portion 15b of the proximal end side portion of the distal end portion 5 has been fitted into the distal end side portion of the bending portion 6, enlargement of the outside diameter of the distal end side of the insertion portion 3 can also be prevented.

[Second Embodiment]

Figure 4:
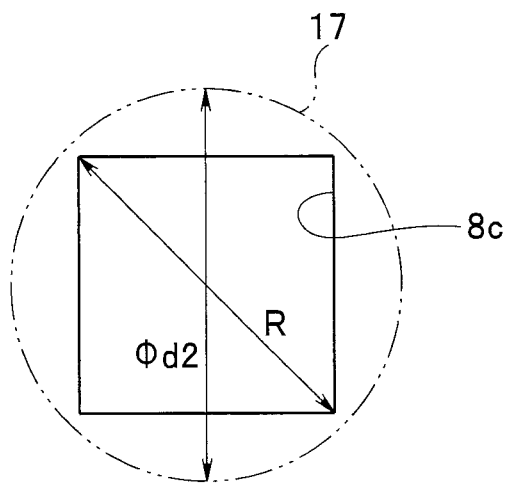
FIG. 4 is a view that illustrates one configuration example of a hole according to a second embodiment of the present invention.
Figure 5:
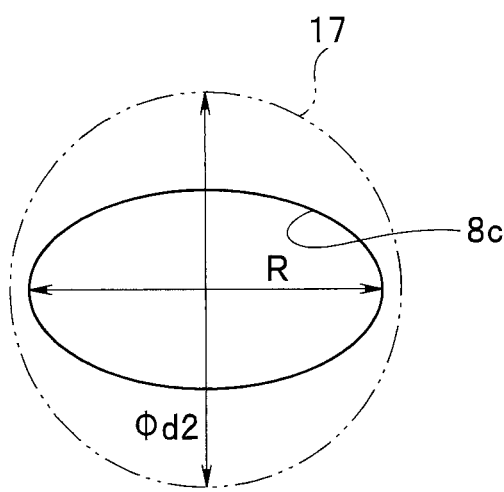
FIG. 5 is a view that illustrates another configuration example of a hole according to the second embodiment.
Figure 6:
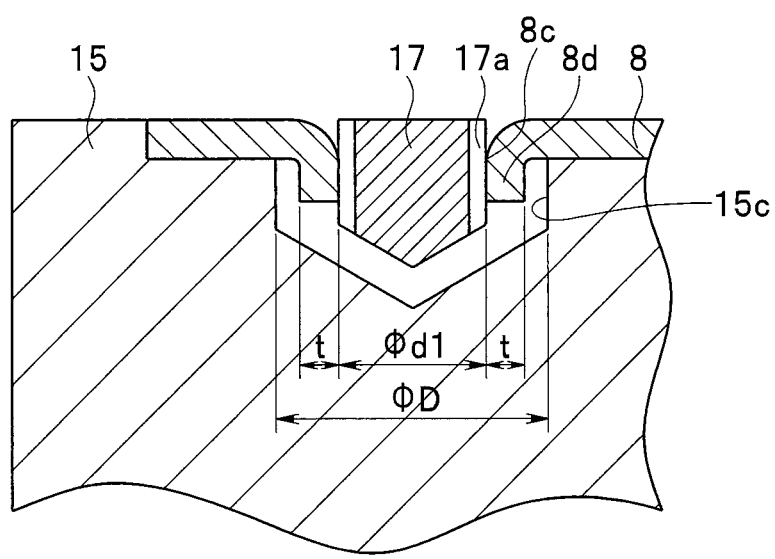
FIG. 6 is a cross-sectional view that illustrates a state when a screw member has been screw-fastened into the hole according to the second embodiment.

FIG. 4 to FIG. 6 illustrate a second embodiment of the present invention. FIG. 4 is a view that illustrates one example of the configuration of the hole 8c. FIG. 5 is a view that illustrates another example of the configuration of the hole 8c. FIG. 6 is a cross-sectional view that illustrates a state when the screw member 17 has been screw-fastened into the hole 8c.

In the description of the second embodiment, portions that are the same as in the foregoing first embodiment are denoted by the same reference characters and a description of such portions is omitted, and primarily only differences relative to the first embodiment are described.

Although the hole 8c was formed as a circular hole in the above described first embodiment, in the present embodiment the hole 8c is formed in a shape that is different to a circular shape.

That is, in the example shown in FIG. 4, the hole 8c is formed as a rectangular hole (for example, a square hole). Although a maximum diameter R of the hole 8c is a diagonal line in a case where the hole 8c is a rectangular hole, a configuration is adopted so that the maximum diameter R is smaller than the root diameter $\Phi d2$ of the screw thread 17a of the screw member 17 (R<$\Phi d2$).

Further, in the example shown in FIG. 5, the hole 8c is formed as an elliptical hole. Although the maximum diameter R is the long diameter in a case where the hole 8c is an elliptical hole, in this example also a configuration is adopted so that the maximum diameter R is smaller than the root diameter $\Phi d2$ of the screw thread 17a of the screw member 17 ($R<\Phi d2$).

When the screw member 17 is screw-fastened into the hole 8c having the above configuration, because the cross-section of the screw member 17 is larger than the cross-section of the hole 8c, the screw member 17 is necessarily inserted with force into the hole 8c. When forcibly inserting the screw member 17, a greater amount of stress is applied to portions that are closer to the axial center, i.e. middle portions of the sides of the quadrangle in the example shown in FIG. 4 and the minor axis sides of the ellipse in the example shown in FIG. 5.

As the result of forcibly inserting the screw member 17 into the hole 8c in this manner, an edge where the hole 8c is formed in the bending portion 6 (in particular, an edge at which a greater amount of stress is applied as described above) bends in the screw-fastening direction of the screw member 17 and, as shown in FIG. 6, a curved portion 8d is formed.

As a result, the hole 8c changes shape into an approximately circular shape along the outer circumference of the screw member 17, and a grip length between the screw member 17 and the bending portion 6 increases at the curved portion 8d. Accordingly, because the grip length increases, the screw-fastening between the screw member 17 and the bending portion 6 can be made more secure.

When adopting this configuration, from the viewpoint of not applying stress to the holding member 15, it is preferable that the curved portion 8d also does not contact the concave portion 15c of the holding member 15. Accordingly, it is preferable to make the diameter $\Phi D$ of the concave portion 15c greater than a length obtained by adding together the outside diameter $\Phi d1$ of the screw thread 17a and an amount obtained by doubling the thickness t of the distal end side portion of the bending portion 6 in which the hole 8c is provided. That is, it is good to satisfy the relationship of the following expression (5).

$$\Phi D > (2 \times t + \Phi d1) \quad \text{[Expression 5]}$$

Note that although a rectangular hole that has a square shape is illustrated as an example in FIG. 4, more generally, the hole 8c may be a polygonal hole. Further, the hole 8c is not limited to a polygonal hole or the elliptical hole that is shown in FIG. 5, and a configuration may also be adopted in which the hole 8c has a more complex shape, for example, the hole 8c may have a shape of a closed curve that is formed with a free-form curve. Whichever shape the hole 8c has, it is good if an area in a plane perpendicular to the depth direction of the hole 8c is less than a circular area constituted by the root diameter $\Phi d2$ of the screw thread 17a. More preferably, it is good for the maximum diameter of the hole 8c to be less than the root diameter $\Phi d2$ of the screw thread 17a (that is, for a closed curve defining the shape of the hole 8c to fall within a circle constituted by the root diameter $\Phi d2$ of the screw thread 17a).

According to the second embodiment configured as described above, in addition to attaining approximately the same effects as in the above described first embodiment, because the hole 8c is a non-circular hole that is formed in a size such that the screw member 17 is forcibly inserted therein, the curved portion 8d can be formed at the edge thereof and the screw-fastening can be made more secure.

Note that the present invention is not limited to the precise embodiments described above, and can be embodied in the implementing stage by modifying the components without departing from the scope of the invention. Also, various aspects of the invention can be formed by appropriately combining a plurality of the components disclosed in the embodiments described above. For example, some components may be deleted from all of the disclosed components according to the embodiments. Furthermore, components from different embodiments may be appropriately combined. Thus, naturally various modifications and applications are possible within a range that does not deviate from the spirit and scope of the present invention.

What is claimed is:

1. An endoscope, comprising:
   an insertion portion that is insertable into an observation object;
   a bending portion having a bendable tubular structure that is provided in the insertion portion;
   a holding member that is provided at a position that is further on a distal end side than the bending portion, and is used for holding an observation portion that observes the observation object;
   a contact portion that is positioned in a distal end side portion of the bending portion, and that contacts a proximal end side portion of the holding member as a result of the proximal end side portion of the holding member being fitted into an inside surface thereof;
   a wall defining a hole portion formed in the contact portion, the hole portion being provided in the distal end side portion of the bending portion;
   a concave portion formed in the proximal end side portion of the holding member at a position corresponding to the hole portion; and
   a screw member that penetrates the wall defining the hole portion by screw-fastening, a distal end side of the screw member being housed in the concave portion;
   wherein:
   a diameter in a direction perpendicular to a depth direction of the concave portion is larger than an outside diameter of the screw member,
   a length, in the depth direction, obtained by adding a depth of the concave portion in the depth direction and a thickness of the wall defining the hole portion in the depth direction is greater than an axial direction length of the screw member;
   the diameter of the concave portion is greater than a diameter of the hole portion in the direction perpendicular to the depth direction; and
   no portions of the screw member, after the screw-fastening, contact with portions defining the concave portion.

2. The endoscope according to claim 1, wherein the contact portion is joined to the holding member by an adhesive.

3. The endoscope according to claim 1, wherein a maximum diameter of the hole portion before screw-fastening by means of the screw member is smaller than a root diameter of the screw member.

4. The endoscope according to claim 3, wherein:
   the hole portion before screw-fastening by means of the screw member is formed as a polygonal hole or an elliptical hole; and
   by screw-fastening the screw member into the hole portion, the hole portion changes shape into an approximately circular shape and at least a portion of the walls defining the hole portion are deformed into the concave portion in the depth direction.

5. The endoscope according to claim 4, wherein no portions of the walls deformed into the concave portion contact with the portions defining the concave portion.

6. The endoscope according to claim 1, wherein the holding member is formed of a resin.

* * * * *